(12) United States Patent
Malinowski et al.

(10) Patent No.: US 10,814,136 B2
(45) Date of Patent: Oct. 27, 2020

(54) TOOLLESS CONNECTOR FOR LATCHING STIMULATION LEADS AND METHODS OF MAKING AND USING

(71) Applicant: Boston Scientific Neuromodulation Corporation, Valencia, CA (US)

(72) Inventors: Zdzislaw Bernard Malinowski, Castaic, CA (US); Jeffery Van Funderburk, Stevenson Ranch, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 157 days.

(21) Appl. No.: 15/905,499

(22) Filed: Feb. 26, 2018

(65) Prior Publication Data

US 2018/0243570 A1     Aug. 30, 2018

Related U.S. Application Data

(60) Provisional application No. 62/464,710, filed on Feb. 28, 2017.

(51) Int. Cl.
*A61N 1/37* (2006.01)
*A61N 1/375* (2006.01)
*A61N 1/05* (2006.01)

(52) U.S. Cl.
CPC ............. *A61N 1/3752* (2013.01); *A61N 1/05* (2013.01)

(58) Field of Classification Search
USPC ................................................. 607/116, 117
See application file for complete search history.

(56) References Cited

U.S. PATENT DOCUMENTS 3,222,471 A    12/1965  Steinkamp
3,601,747 A     8/1971  Prall et al.
(Continued)

FOREIGN PATENT DOCUMENTS

EP    0580928 A1    2/1994
EP    0650694 B1    7/1998
(Continued)

OTHER PUBLICATIONS

International Search Report and Written Opinion for PCT Application No. PCT/US2018/019752 dated Jun. 11, 2018.

*Primary Examiner* — Nicole F Lavert
(74) *Attorney, Agent, or Firm* — Lowe Graham Jones PLLC; Bruce E. Black

(57) ABSTRACT

An electrical stimulation lead latching kit includes a connector having a housing that defines a lead lumen and a latching lumen that at least partially intersects the lead lumen; and a latching device including a latching pin, a handle, and an attaching element that attaches the latching pin to the handle. The latching pin has a longitudinal surface and is configured for insertion into the latching lumen, and the attaching element is configured to enable the latching pin to detach from the handle when the latching pin is in the latching lumen. When the latching pin is positioned in the latching lumen and a portion of an electrical stimulation lead or lead extension is positioned in the lead lumen, the longitudinal surface of the latching pin engages the electrical stimulation lead or lead extension to latch the electrical stimulation lead or lead extension to the connector.

18 Claims, 9 Drawing Sheets

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,262,673 A * | 4/1981 | Kinney ............. A61N 1/3752 607/36 |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffmann et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,575,759 B1 | 6/2003 | Ollivier |
| 6,604,283 B1 | 8/2003 | Kuzma |
| 6,605,094 B1 | 8/2003 | Mann et al. |
| 6,609,029 B1 | 8/2003 | Mann et al. |

(56) References Cited

U.S. PATENT DOCUMENTS

| | | |
|---|---|---|
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooj et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 4/2009 | Marvin et al. |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B2 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0055062 A1 | 3/2005 | Correas et al. |
| 2005/0137665 A1 | 6/2005 | Cole |

(56) References Cited

U.S. PATENT DOCUMENTS

| | | |
|---|---|---|
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0270940 A1 | 10/2009 | Deininger et al. |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffitt et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |

(56) References Cited

FOREIGN PATENT DOCUMENTS

| | | |
|---|---|---|
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

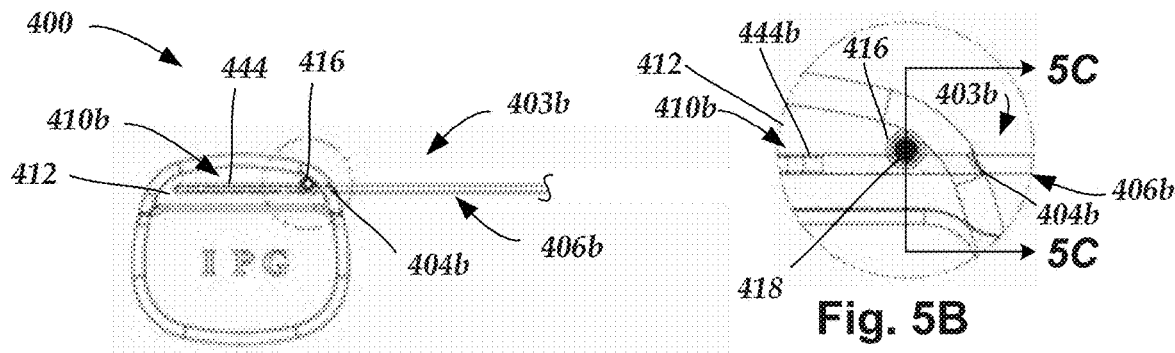
Fig. 5A
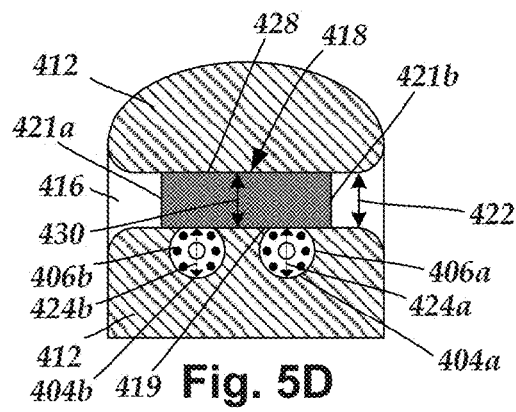
Fig. 5B
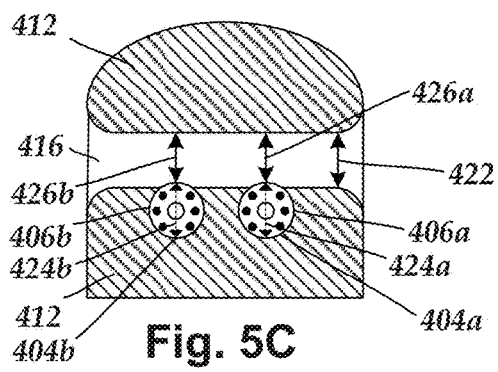
Fig. 5C
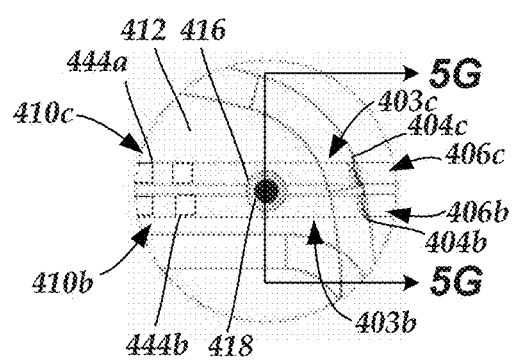
Fig. 5D
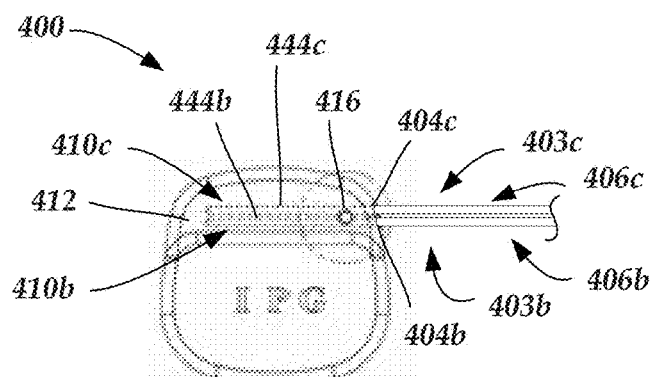
Fig. 5E
Fig. 5F
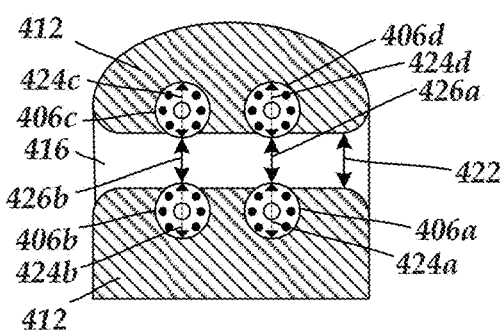
Fig. 5G
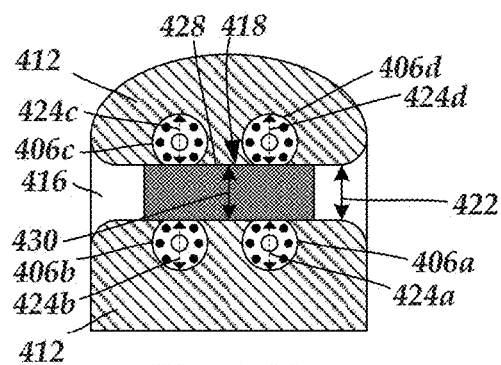
Fig. 5H

TOOLLESS CONNECTOR FOR LATCHING STIMULATION LEADS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/464,710, filed Feb. 28, 2017, which is incorporated herein by reference.

FIELD

The present invention is directed to the area of implantable electrical stimulation systems and methods of making and using the systems, and in particular connectors for latching stimulation leads and methods of making and using the connectors.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead latching kit that includes a connector having a housing that defines a lead lumen and a latching lumen that at least partially intersects the lead lumen to receive a portion of an electrical stimulation lead or lead extension; and a latching device including a latching pin, a handle, and an attaching element that attaches the latching pin to the handle. The latching pin has a longitudinal surface and is configured for insertion into the latching lumen, and the attaching element is configured to enable the latching pin to detach from the handle when the latching pin is in the latching lumen. The latching pin has a cross-sectional dimension so that, when the latching pin is positioned in the latching lumen and the portion of the electrical stimulation lead or lead extension is positioned in the lead lumen, the longitudinal surface of the latching pin engages the portion of the electrical stimulation lead or lead extension to latch the electrical stimulation lead or lead extension to the connector.

In at least some embodiments, the attaching element is a frangible portion between the latching pin and the handle. In at least some embodiments, the housing of the connector includes at least two lead lumens that each at least partially intersect the latching lumen. In at least some embodiments, the latching pin is cylindrical. In at least some embodiments, the latching pin is a modified cylinder with a rounded, longitudinal surface and one flat, longitudinal surface.

In at least some embodiments, the latching lumen has a longitudinal dimension that is at least as long as a longitudinal dimension of the latching pin. In at least some embodiments, the latching pin has a tapered proximal end portion. In at least some embodiments, at least one portion of the latching lumen is threaded and a portion of the latching pin is also threaded. In at least some embodiments, an end of the latching pin includes a recess configured to receive an end portion of a tool. In at least some embodiments, the housing includes another lead lumen that at least partially intersects the latching lumen and is disposed opposite the lead lumen with the latching lumen between the lead lumen and the other lead lumen.

In at least some embodiments, the latching pin has the cross-sectional dimension so that, when the latching pin is positioned in the latching lumen and the portion of the electrical stimulation lead or lead extension is positioned in the lead lumen, the latching pin compresses the portion of the electrical stimulation lead or lead extension to latch the electrical stimulation lead or lead extension to the connector. In at least some embodiments, the housing of the connector includes another latching lumen that at least partially intersects the lead lumen.

In at least some embodiments, the electrical stimulation lead latching kit further includes the electrical stimulation lead which has a lead body having a distal end portion, a proximal end portion, and a longitudinal length; electrodes disposed along the distal end portion of the lead body; terminals disposed along the proximal end portion of the lead body; and conductors electrically coupling the terminals to the electrodes.

In at least some embodiments, the electrical stimulation lead latching kit further includes a control module wherein the control module includes the connector. In at least some embodiments, the electrical stimulation lead latching kit further includes a pin disposal tool that includes a housing, the housing of the pin disposal tool including a control module lumen and a pin catching compartment that extends from the control module lumen, wherein the control module lumen is configured to receive the housing of the connector, wherein the pin catching compartment is configured to at least partially align with the latching lumen of the housing of the connector when the control module lumen receives the housing of the connector, wherein the pin catching compartment is further configured to receive the latching pin from the latching lumen of the housing of the connector when the pin catching compartment at least partially aligns with the latching lumen of the housing of the connector.

In at least some embodiments, the electrical stimulation lead latching kit further includes a lead extension, wherein the lead extension includes the connector. In at least some embodiments, the electrical stimulation lead latching kit further includes a lead anchor, wherein the lead anchor includes the connector.

Another embodiment is a method of latching an electrical stimulation lead or lead extension using any of the electrical stimulation lead latching kits described above. The method includes inserting a portion of the electrical stimulation lead or lead extension into the lead lumen of the housing of the connector of the electrical stimulation lead latching kit; inserting the latching pin of the latching device into the latching lumen of the housing of the connector to engage the electrical stimulation lead or lead extension to latch the electrical stimulation lead or lead extension to the connector;

and detaching the latching pin from the handle while the latching pin is positioned in the latching lumen.

A further embodiment is a method of unlatching an electrical stimulation lead or lead extension using the electrical stimulation lead latching kit with the pin disposal tool described above. The method includes providing the control module of the electrical stimulation lead latching kit with a portion of the lead or lead extension inserted in the lead lumen and the latching pin disposed in the latching lumen and engaging the portion of the electrical stimulation lead or lead extension; inserting the housing of the connector into the control module lumen of the pin disposal tool to at least partially align the pin catching compartment of the pin disposal tool with the latching lumen of the housing of the connector; and pushing the latching pin from the latching lumen into the pin catching compartment of the pin disposal tool to disengage the latching pin from the portion of the electrical stimulation lead or lead extension to unlatch the electrical stimulation lead or lead extension.

Yet another embodiment is a connector that includes a housing that defines a lead lumen and a latching lumen that at least partially intersects the lead lumen, where the lead lumen is configured to receive a portion of an electrical stimulation lead or lead extension; and a latching pin disposed in the latching lumen. The latching pin has a longitudinal surface configured for rotation between an unlocked position and a locked position. In the unlocked position, the connector is configured for insertion or removal of a portion of the electrical stimulation lead or lead extension from the lead lumen and, in the locked position with the portion of the electrical stimulation lead or lead extension disposed in the lead lumen, the longitudinal surface of the latching pin engages the portion of the electrical stimulation lead or lead extension to latch the electrical stimulation lead or lead extension to the connector.

In at least some embodiments, the housing of the connector includes at least two lead lumens that each at least partially intersect the latching lumen. In at least some embodiments, the latching pin is a modified cylinder with a rounded, longitudinal surface and one flat, longitudinal surface. In at least some embodiments, the latching lumen has a longitudinal dimension that is at least as long as a longitudinal dimension of the latching pin. In at least some embodiments, the latching pin has a tapered proximal end portion. In at least some embodiments, at least one portion of the latching lumen is threaded and a portion of the latching pin is also threaded. In at least some embodiments, an end of the latching pin includes a recess configured to receive an end portion of a tool.

In at least some embodiments, the latching pin has the cross-sectional dimension so that, when the portion of the electrical stimulation lead or lead extension is positioned in the lead lumen and the latching pin is in the locked position, the latching pin compresses the portion of the electrical stimulation lead or lead extension to latch the electrical stimulation lead or lead extension to the connector.

In at least some embodiments, the connector is part of a control module. In at least some embodiments, the connector is part of a lead extension. In at least some embodiments, the connector is part of a lead anchor.

Another embodiment is a system that includes the connector and an electrical stimulation lead which has a lead body having a distal end portion, a proximal end portion, and a longitudinal length; electrodes disposed along the distal end portion of the lead body; terminals disposed along the proximal end portion of the lead body; and conductors electrically coupling the terminals to the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic side view of one embodiment of the lead latching kit of FIG. 4A, according to the invention;

FIG. 5B is a schematic expanded view of one embodiment of the circled portion of FIG. 5A, according to the invention;

FIG. 5C is a schematic lateral cross-sectional view of one embodiment of the lead latching kit of FIG. 5B taken at line 5C-5C without the latching pin, according to the invention;

FIG. 5D is a schematic lateral cross-sectional view of one embodiment of the lead latching kit of FIG. 5B taken at line 5C-5C with the latching pin in the connector housing, according to the invention;

FIG. 5E is a schematic side view of another embodiment of the lead latching kit of FIG. 4A, according to the invention;

FIG. 5F is a schematic expanded view of one embodiment of the circled portion of FIG. 5E, according to the invention;

FIG. 5G is a schematic lateral cross-sectional view of one embodiment of the lead latching kit of FIG. 5F taken at line 5G-5G without the latching pin, according to the invention;

FIG. 5H is a schematic lateral cross-sectional view of one embodiment of the lead latching kit of FIG. 5F taken at line 5G-5G with the latching pin in the connector housing, according to the invention;

DETAILED DESCRIPTION

The present invention is directed to the area of implantable electrical stimulation systems and methods of making and using the systems, and in particular connectors for latching stimulation leads and methods of making and using the connectors.

Suitable implantable electrical stimulation systems include, but are not limited to, a least one lead with at least one electrode disposed along a distal end of the lead and at least one terminal disposed along the at least one proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1:
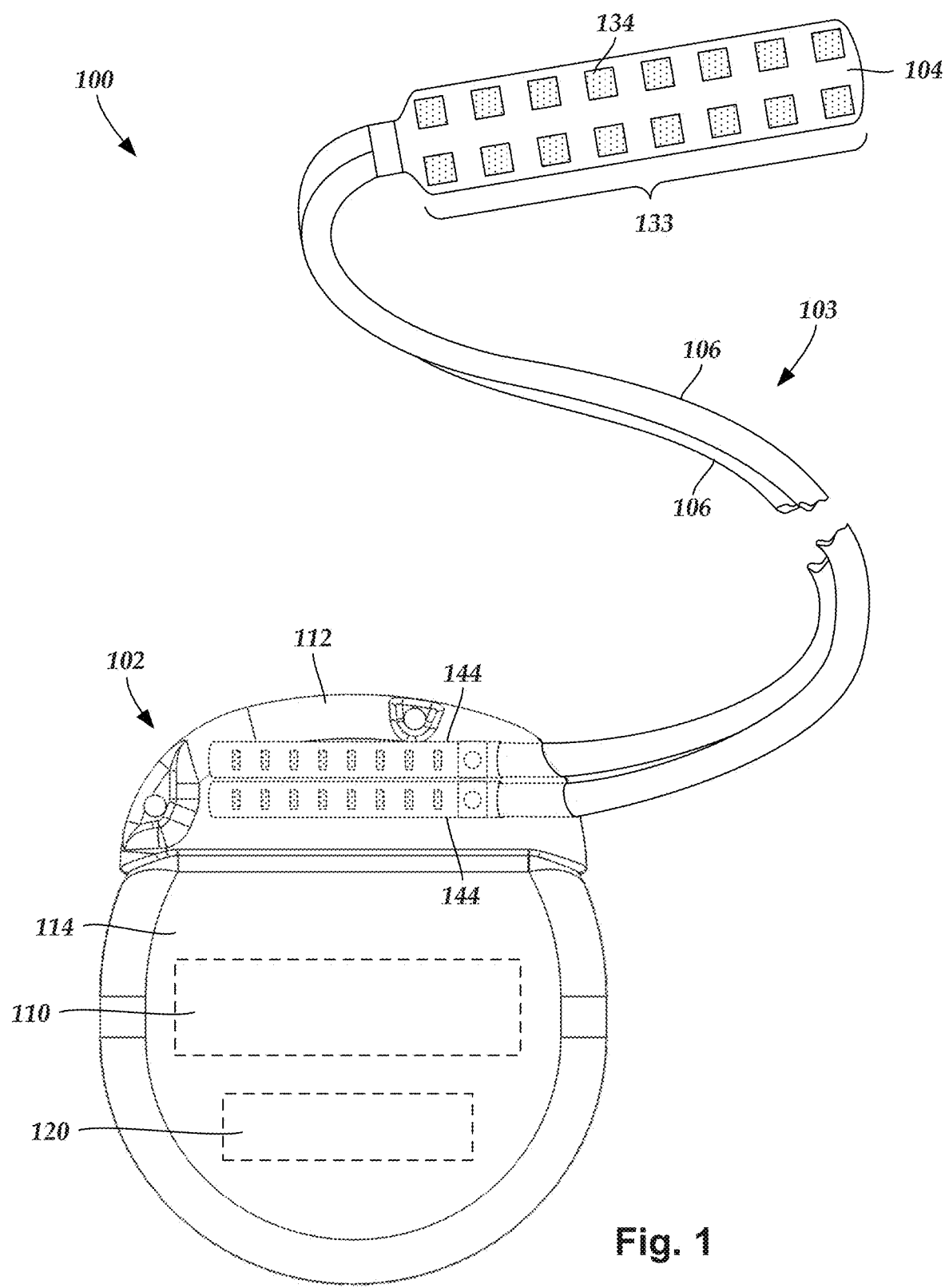
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (for example, a stimulator or pulse generator) 102 and a lead 103 coupleable to the control module 102. The lead 103 includes a paddle body 104 and at least one lead body 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (for example, 310 in FIG. 3A) is disposed along each of the at least one lead body 106. In at least some embodiments, there may be a single electrode 134 or a single terminal.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
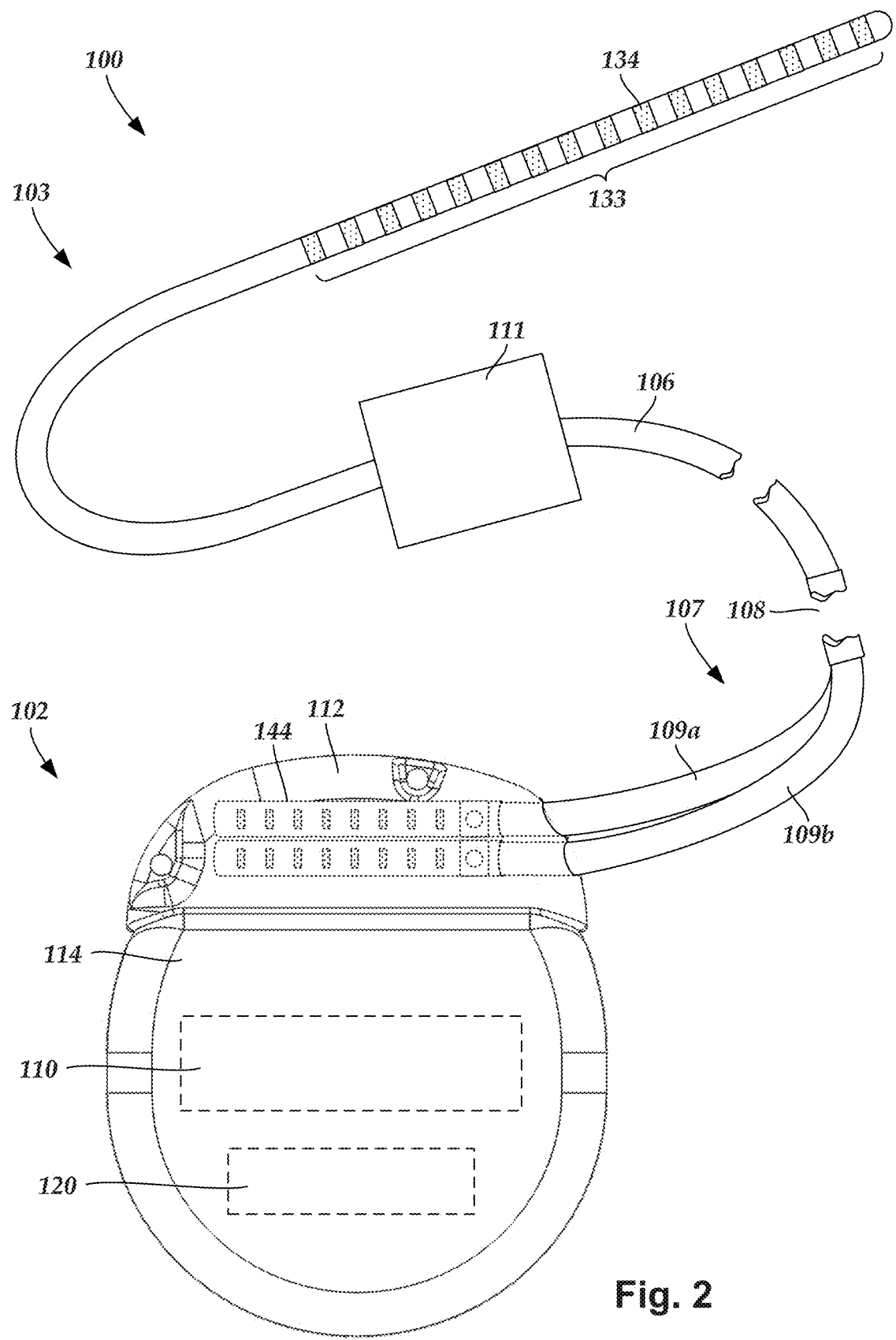
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the at least one lead body 106. In at least some embodiments, the lead 103 is isodiametric along a longitudinal length of the lead body 106. FIG. 2 also illustrates a lead anchor 111 disposed around a portion of the lead 103 to anchor the lead to surrounding tissue. The lead anchor 111 has a connector with a lead lumen that receives a portion of the lead and a fastener to attach the lead anchor to the lead.

The lead 103 can be coupled to the control module 102 in any suitable manner. In FIG. 1, the lead 103 is shown coupling directly to the control module 102. In at least some other embodiments, the lead 103 couples to the control module 102 via at least one intermediate device (324 in FIG. 3B). For example, in at least some embodiments at least one lead extension 324 (see, for example, FIG. 3B) can be disposed between the lead 103 and the control module 102 to extend the distance between the lead 103 and the control module 102. Other intermediate devices may be used in addition to, or in lieu of, at least one lead extension including, for example, a splitter, an adaptor, or the like or combinations thereof. It will be understood that, in the case where the electrical stimulation system 100 includes multiple intermediate devices disposed between the lead 103 and the control module 102, the intermediate devices may be configured into any suitable arrangement.

In FIG. 2, the electrical stimulation system 100 is shown having a splitter 107 configured for facilitating coupling of the lead 103 to the control module 102. The splitter 107 includes a splitter connector 108 configured to couple to a proximal end of the lead 103, and at least one splitter tail 109a and 109b configured to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured to make an electrical connection between the lead 103 and the electronic subassembly 110 of the control module 102.

The electrical stimulation system 100 or components of the electrical stimulation system 100, including the paddle body 104, the at least one of the lead bodies 106, and the control module 102, are typically implanted into the body of a patient. The electrical stimulation system 100 can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, at least one of the electrodes 134 are formed from at least one of: platinum, platinum iridium, palladium, palladium rhodium, or titanium.

Any suitable number of electrodes 134 can be disposed on the lead 103 including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes 134 of the paddle body 104 (or at least one lead body 106) are typically disposed in, or separated by, a non-conductive, biocompatible material such as, for example, silicone, polyurethane, polyetheretherketone ("PEEK"), epoxy, and the like or combinations thereof. The at least one lead body 106 and, if applicable, the paddle body 104 may be formed in the desired shape by any process including, for example, molding (including injection molding), casting, and the like. The non-conductive material typically extends from the distal ends of the at least one lead body 106 to the proximal end of each of the at least one lead body 106.

In the case of paddle leads, the non-conductive material typically extends from the paddle body 104 to the proximal end of each of the at least one lead body 106. Additionally, the non-conductive, biocompatible material of the paddle body 104 and the at least one lead body 106 may be the same or different. Moreover, the paddle body 104 and the at least one lead body 106 may be a unitary structure or can be formed as two separate structures that are permanently or detachably coupled together.

Figure 3A:
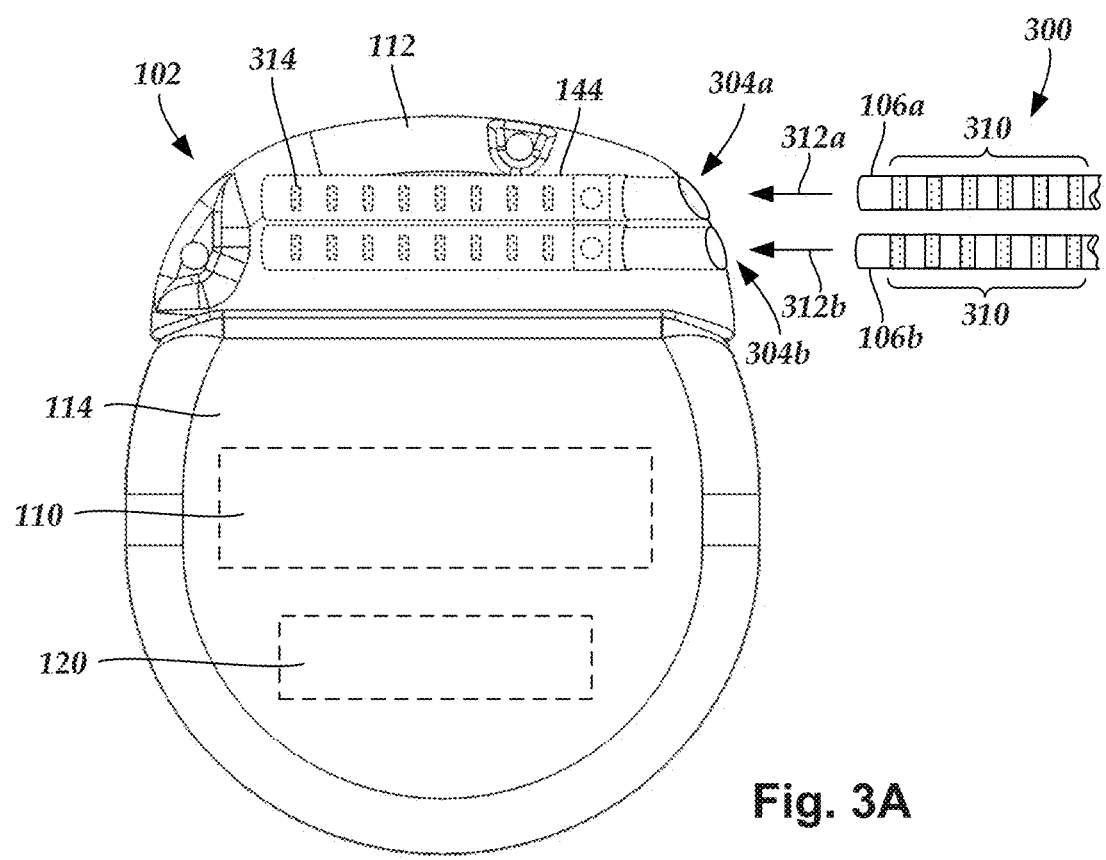
FIG. 3A is a schematic side view of one embodiment of the control module of FIG. 1 configured to electrically couple to a lead body, according to the invention.

Terminals (for example, 310 in FIG. 3A) are typically disposed along the proximal end of the at least one lead body 106 of the electrical stimulation system 100 (as well as any splitters, lead extensions, adaptors, or the like) for electrical connection to corresponding connector contacts (for example, 314 in FIG. 3A). The connector contacts are disposed in connectors (for example, 144 in FIGS. 1-3B; and 322 in FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, at least one electrode 134 are electrically coupled to each terminal. In at least some embodiments, each terminal is only connected to one electrode 134.

FIG. 3A is a schematic side view of one embodiment of a proximal end of at least one elongated device 300 configured for coupling to one embodiment of the control module connector 144. The at least one elongated device 300 may include, for example, at least one of the lead bodies 106 of FIG. 1, at least one intermediate device (for example, a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports. Each port is an opening to a lead lumen within which a portion of the lead can be inserted.

The control module connector 144 also includes a plurality of connector contacts, such as connector contact 314, disposed within the lead lumen associated with each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
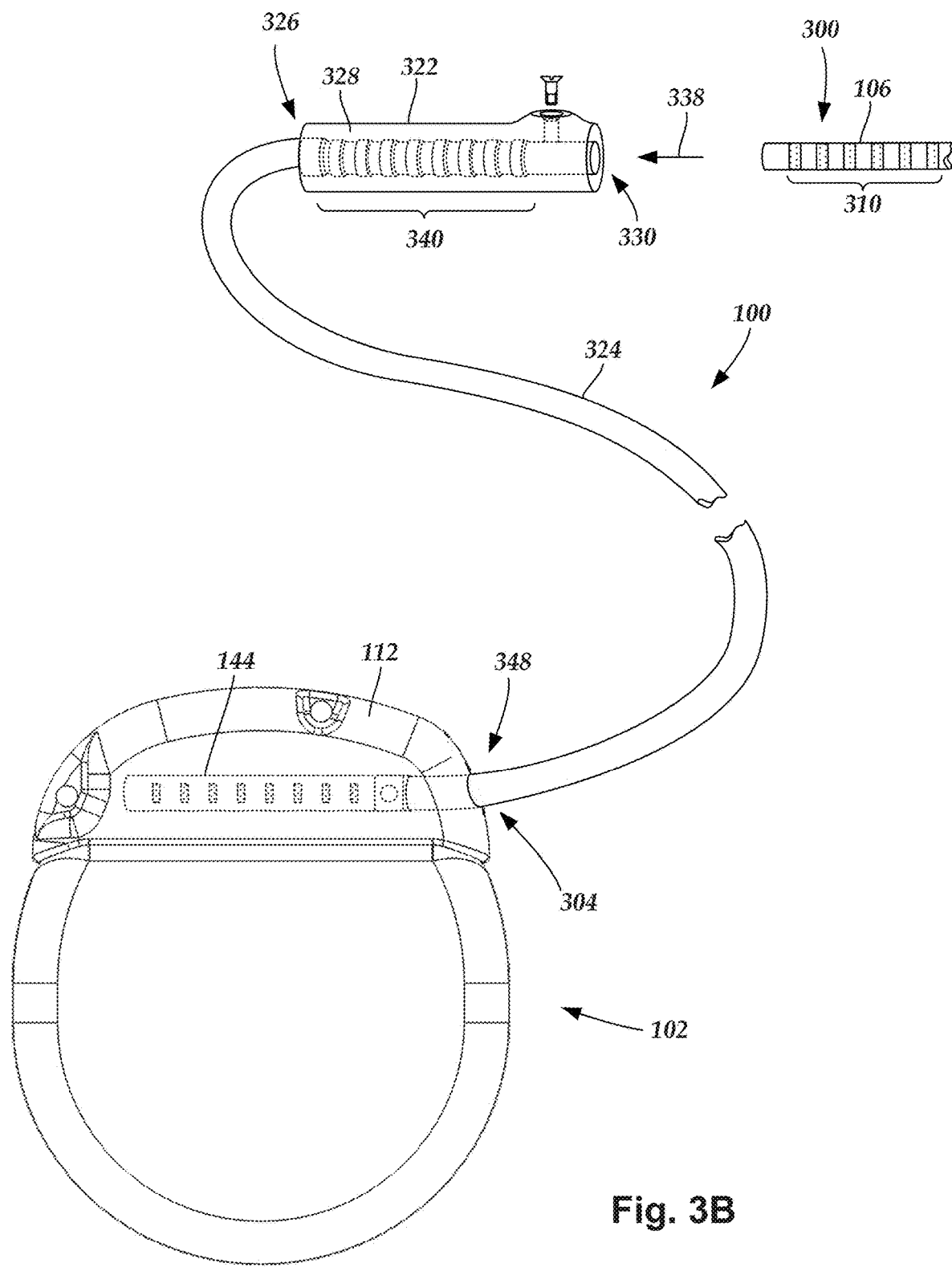
FIG. 3B is a schematic side view of one embodiment of a lead extension configured to electrically couple a lead body to a control module, according to the invention.

FIG. 3B is a schematic side view of another embodiment of the electrical stimulation system 100. The electrical stimulation system 100 includes a lead extension 324 that is configured to couple at least one elongated device 300 (for example, one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured to couple to a single elongated device 300. In alternate embodiments, the lead extension 324 is configured to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 and associated lead lumen into which terminals 310 of the elongated device 300 can be inserted, as shown by directional arrow 338. The connector housing 328 also includes a plurality of connector contacts, such as connector contacts 340. When the elongated device 300 is inserted into the port 330 and its associated lead lumen, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured for insertion into a connector disposed in another lead extension (or another intermediate device). In other embodiments (and as shown in FIG. 3B), the proximal end 348 of the lead extension 324 is configured for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Figure 4A:
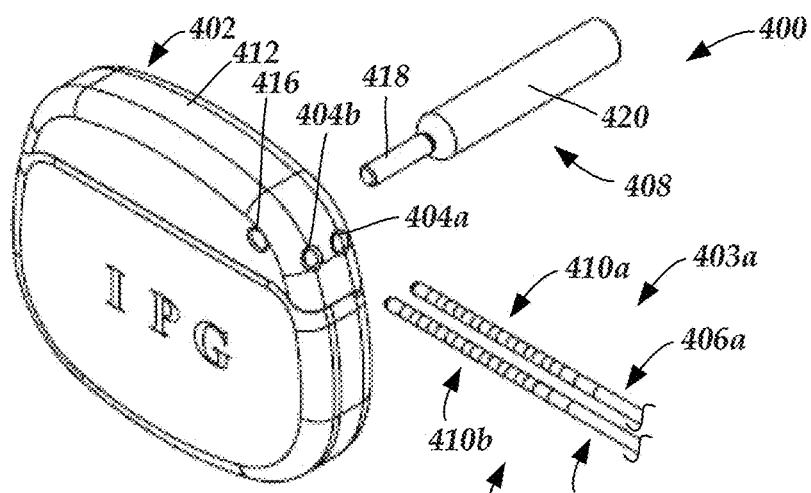
FIG. 4A is a schematic isometric view of one embodiment of a lead latching kit, including a control module and a latching device that has a latching pin attached to a handle, along with a pair of leads, according to the invention.
Figure 4B:
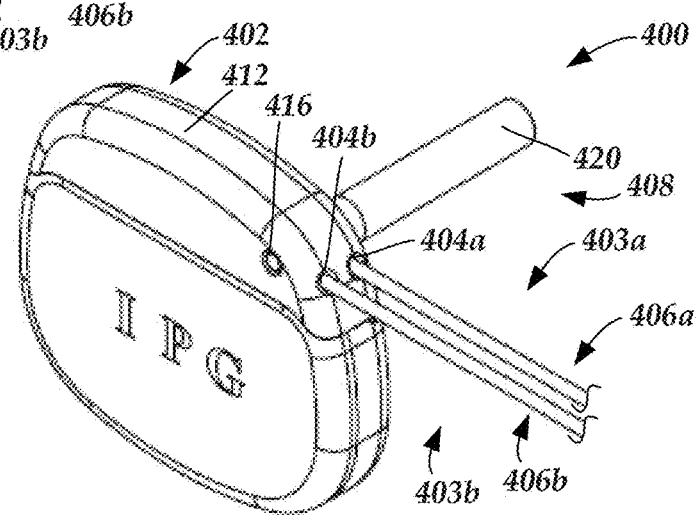
FIG. 4B is a schematic isometric view of one embodiment of the lead latching kit of FIG. 4A, with the leads and the latching pin inserted into a connector housing of the control module, according to the invention.

FIG. 4A is a schematic isometric view of one embodiment of a lead latching arrangement 400 that includes a control module 402 and a latching device 408. The control module includes at least one lead lumen (for example, lead lumens 404a, 404b) for receiving at least one lead (for example, leads 403a, 403b). When terminals 410a, 410b of the leads 403a, 403b are received in the connector housing 412 of the control module 402, the latching device 408 can be inserted into a latching lumen 416 in the connector housing 412 to latch the leads 403a, 403b (FIG. 4B).

Figure 4C:
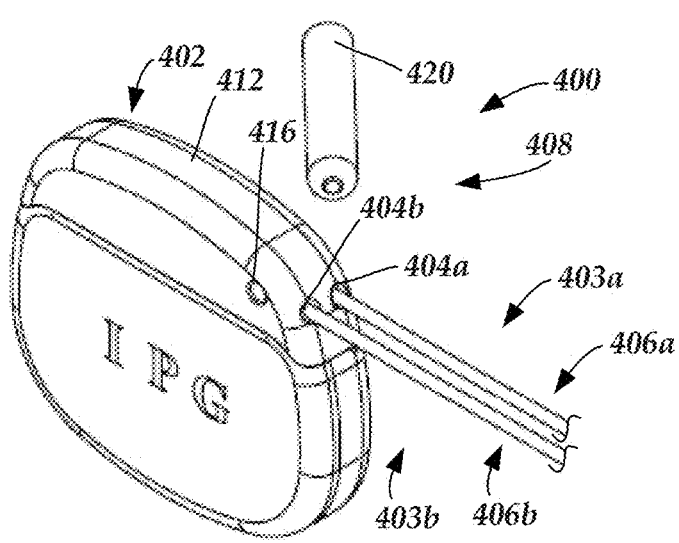
FIG. 4C is a schematic isometric view of one embodiment of the lead latching kit of FIG. 4A, with the handle detached from the latching pin, according to the invention.

The latching device 408 includes a handle 420 and a latching pin 418 attached to the proximal end of the handle 420. After the latching pin 418 has been inserted into the latching lumen 416, a user can apply torque to the distal end portion of the handle 420 to detach the handle 420 from the latching pin 418 (FIG. 4C).

FIG. 5A is a schematic side view of one embodiment of the lead latching arrangement 400 with a partially transparent view of the connector housing 412 and connector 444. FIG. 5B is a schematic expanded view of one embodiment of the circled portion of FIG. 5A. The latching lumen 416 at least partially intersects the lead lumen 404b (only one shown) to enable the latching pin 418 in the latching lumen 416 to frictionally engage or compress the lead body 406b (only one shown) in the lead lumen 404b to latch the lead 403b while the lead terminals 410b electrically couple to connector contacts disposed in the connector 444 in the connector housing 412.

FIG. 5C is a schematic lateral cross-sectional view of one embodiment of the lead latching arrangement 400 taken at line 5C-5C. When the latching pin 418 is absent from the latching lumen 416, the non-compressed lead bodies 406a, 406b have cross-sectional dimensions 424a, 424b that can extend into the latching lumen 416, thereby reducing cross-sectional dimensions 426a, 426b of free space above the lead bodies 406a, 406b in the latching lumen 416. The cross-sectional dimensions 426a, 426b of free space may be smaller than at least one cross-sectional dimension 430 of the body 428 of the latching pin 418. When the latching lumen 416 receives the latching pin 418, the latching pin body 428 may frictionally engage or compress the lead bodies 406a, 406b to latch the leads 403a, 403b (FIG. 5D). In at least some embodiments, the cross-sectional dimension 430 of the latching pin body 428 may be at least as large as a cross-sectional dimension 422 of the latching lumen 416 to facilitate retention of the latching pin 418 in the latching lumen 416. In at least some embodiments, the latching lumen 416 may be wider, than the cross-sectional dimension 422, at one or both openings to facilitate insertion of the latching pin 418 into the latching lumen. In at least some embodiments, the latching lumen 416 is open at only one side of the connector housing 412 instead of two sides.

As can be seen in FIG. 5D, the longitudinal surface 419 of the latching pin 418 engages the lead bodies 406a, 406b, not the end surfaces 421a, 421b of the latching pin 418. In contrast, conventional lead fasteners engage the lead with the end surfaces of the fastener which is more likely to damage the lead, particularly if excessive torque is applied to the fastener when it engages the lead. In addition, as can be seen in FIG. 5D, the latching pin 418 extends laterally away from the lead bodies 406a, 406b in both opposing directions. It will be recognized that to accomplish such an arrangement, the central longitudinal axis of the latching lumen 416 does not intersect the central longitudinal axes of the lead lumens 404a, 404b.

In at least some embodiments, the connector housing 412 includes at least one, two, three, four, five, six, seven, or eight latching lumens 416 that each intersect one, two, three, four, five, six, seven, eight or more lead lumens 404. In at least some embodiments, two or more latching lumens 416 intersect at least one same lead lumen 404. In other embodiments, different latching lumens intersect different lead lumens. In at least some embodiments, two or more of the latching lumens 416 are laterally spaced apart and vertically aligned with each other. In at least some embodiments, two or more of the latching lumens 416 are laterally spaced apart and vertically offset from each other. In other embodiments, two or more of the latching lumens 416 are vertically spaced apart and laterally aligned with each other. In at least some embodiments, two or more of the latching lumens 416 are vertically and laterally spaced apart from each other. In at least some embodiments, the latching pin 418, latching lumen 416, and lead lumens 404 may be arranged and configured to facilitate latching leads 403 below, above, or both above and below the latching pin 418. For example, FIG. 5E is a schematic side view of another embodiment of the lead latching arrangement 400 with the latching lumen 416 at least partially intersecting lead lumens 404b, 404c (only two shown) above and below the latching lumen 416 to facilitate latching leads 403b, 403c while the lead terminals 410b, 410c electrically couple to connector contacts disposed in the connector 444 of the connector housing 412. FIG. 5F is an expanded view of one embodiment of the circled portion of FIG. 5E.

FIG. 5G is a schematic lateral cross-sectional view of one embodiment of the lead latching arrangement 400 taken at line 5G-5G with the lead diameters 426a-426d of lead bodies 406a-406d in non-engaged or non-compressed states. FIG. 5H is a schematic lateral cross-sectional view of one embodiment of the lead latching arrangement 400 taken at line 5G-5G with the latching pin 418 frictionally engaging or compressing the lead bodies 406a-406d. In at least some embodiments, pairs of lead lumens 404 are vertically aligned or offset.

Figure 6A:
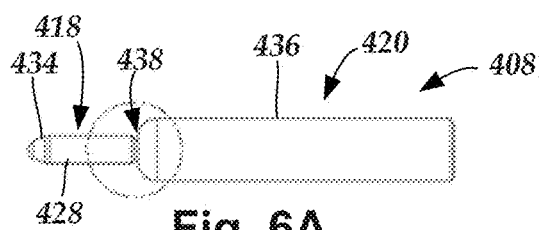
FIG. 6A is a schematic side view of one embodiment of the latching device of FIG. 4A with the latching pin attached to the handle, according to the invention.
Figure 6B:
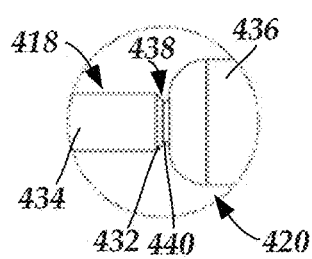
FIG. 6B is a schematic expanded view of one embodiment of the circled portion of FIG. 6A, according to the invention.

FIG. 6A is a schematic side view of one embodiment of the latching device 408 with the latching pin 418 attached to the handle 420. FIG. 6B is an expanded view of one embodiment of the circled portion of FIG. 6A. At least one attaching element 438 may attach the latching pin 418 to the handle 420. The latching pin 418, attaching element 438, and the handle 420 can be made of the same material in a unitary body or can be made of different materials. Examples of suitable materials include, but are not limited to, biocompatible materials, such as polyurethane, polyetheretherketone ("PEEK"), polycarbonate, other polymeric materials, metals, ceramics, or the like. In at least some embodiments, the attaching element 438 is an integral portion of the latching pin 418 and the handle 420 (for example, when formed in a unitary mold, when at least one material is melted to bond the latching pin 418 and the handle 420 to each other, or the like).

Figure 6C:
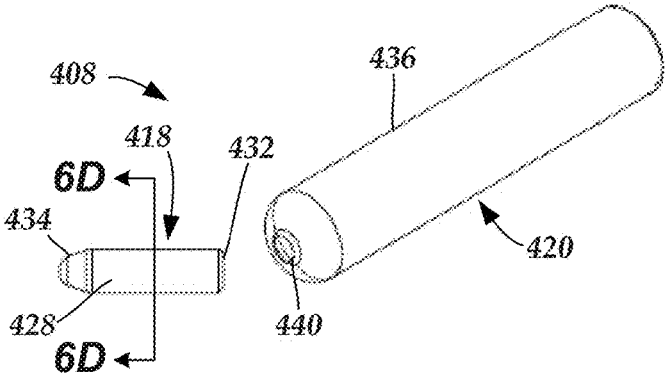
FIG. 6C is a schematic isometric view of one embodiment of the latching device of FIG. 6A with the latching pin detached from the handle, according to the invention.

The attaching element 438 may be a frangible portion to facilitate separating into at least two portions 432, 440 to detach the latching pin 418 from the handle 420 (FIG. 6C). In at least some embodiments, the attaching element 438 has a smaller diameter than the body 434 of the latching pin 434 and the body 436 of the handle 420. In at least some embodiments, the attaching element 438 is at least partially perforated. In other embodiments, the attachment element 438 includes at least one layer of adhesive, such as biocompatible tape, glue, mucilage, paste, or the like. In further embodiments, the attachment element 438 may include at least one magnetic portion, ferromagnetic portion, or the like.

In at least some embodiments, the latching pin 418 has a tapered proximal end portion to facilitate entry into the latching lumen 416. In at least some embodiments, the proximal end portion of the handle 420 has a diameter and length that enables inserting the attached latching pin 418 to a position in the latching lumen 416 that places the portion 432 of the latching pin 418 entirely within the latching lumen 416. In at least some embodiments, the longitudinal length of the latching pin 418 is no larger than the longitudinal length of the latching lumen 416 to reduce the likelihood that, after insertion, either end portion of the latching pin 418 extends out from the connector housing 412. The longitudinal length of the latching pin 418 may be 5, 10, 15, or 20% or more smaller than the longitudinal length of the latching lumen 416.

In at least some embodiments, the distal end portion of the latching device 408 includes another attaching element and latching pin (not shown).

Figure 6D:
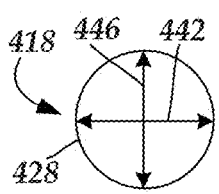
FIG. 6D is a schematic lateral cross-sectional view of one embodiment of the latching pin of FIG. 6C taken at line 6D-6D, according to the invention.
Figure 6E:
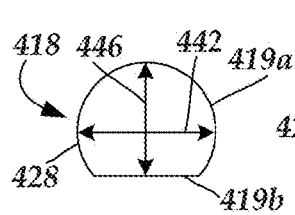
FIG. 6E is a schematic lateral cross-sectional view of another embodiment of the latching pin of FIG. 6C taken at line 6E-6E, according to the invention.
Figure 6F:
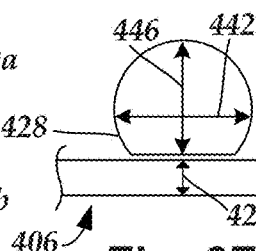
FIG. 6F is a schematic lateral cross-sectional view of one embodiment of the latching pin of FIG. 6E in an unlocked position, according to the invention.
Figure 6G:
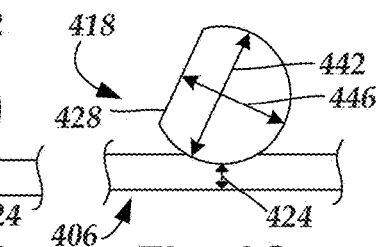
FIG. 6G is a schematic lateral cross-sectional view of one embodiment of the latching pin of FIG. 6E in a locked position, according to the invention.

FIGS. 6D-6G are schematic lateral cross-sectional views of various embodiments of the latching pin 418 taken at line 6D-6D. In at least some embodiments, the body 428 of the latching pin 418 has cross-sectional dimensions 442, 446 that facilitate engaging or compressing a lead body 406 when the latching pin 418 is inserted into the latching lumen 416, regardless of the orientation of the latching pin 418 (FIG. 6D). In FIG. 6D, the latching pin 418 is cylindrical. In other embodiments, the cross-sectional dimensions 442, 446 are different from each other (FIG. 6E) to facilitate inserting the latching pin 418 into the latching lumen 416 in an unlocked position to avoid engaging or compressing the vertical dimension 424 of the lead body 406 (FIG. 6F) and rotating the latching pin to a locked position to engage or compress the vertical dimension 424 of the lead body 406 (FIG. 6G). In FIGS. 6E-6G, the latching pin 418 is a modified cylinder with a rounded, longitudinal surface 419a and one flat, longitudinal surface 419b.

In alternate embodiments, the latching pin 418 has the cross-sectional arrangement illustrated in FIGS. 6E-6G and is part of the connector housing 412, instead of inserted into the using the latching device 408. The latching pin 418 in these embodiments has a slot, other recess, protrusion, or the like at one or both ends that is shaped to engage an end portion of a tool (for example, a slotted, Phillips, Frearson, square, hex, or star male or female screwdriver, wrench, or the like) to turn the latching pin 418 from the unlocked position in FIG. 6F to the locked position in FIG. 6G.

In at least some embodiments, the cross-sectional dimensions of the latching lumen 416 are uniform or vary along the length of the latching lumen 416. In at least some embodiments, at least one end portion of the latching lumen 416 includes a countersink or counterbore. In at least some embodiments, the distal end portion of the latching pin 418 has at least one cross-sectional dimension that is at least as large as the at least one cross-sectional dimension of the proximal end portion of the latching pin 418.

Figure 7A:
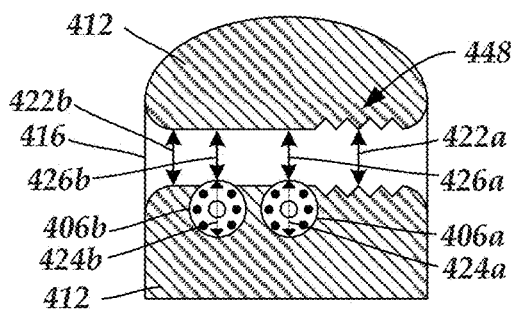
FIG. 7A is a schematic lateral cross-sectional view of another embodiment of the lead latching kit of FIG. 5B taken at line 5C-5C with the latching pin external to the connector housing, according to the invention.
Figure 7B:
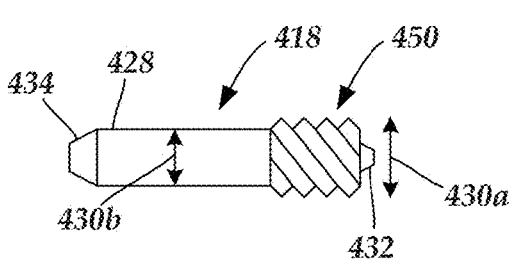
FIG. 7B is a schematic lateral cross-sectional view of a further embodiment of the lead latching kit of FIG. 5B taken at line 5C-5C with the latching pin external to the connector housing, according to the invention.
Figure 7B:
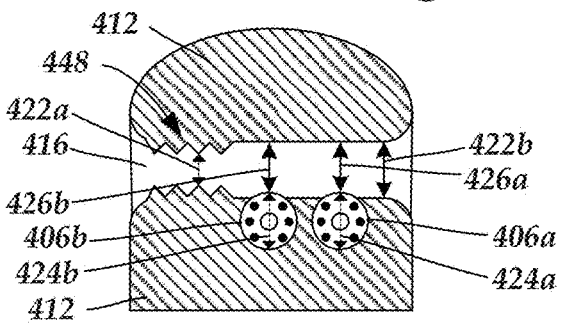

FIGS. 7A and 7B are schematic lateral cross-sectional views of alternative embodiments of the lead latching arrangement 400 taken at line 5C-5C with the latching pin 418 external to the connector housing 412. In at least some embodiments, the latching lumen 416 includes a threaded portion 448, and the latching pin 418 includes a corresponding threaded portion 450 at the distal end portion (FIG. 7A) or the proximal end portion (FIG. 7B). In at least some embodiments, the threaded portions 448, 450 include straight or tapered threads. In at least some embodiments, the threaded portion 448 has a cross-sectional dimension 422a between opposing ridge peaks that is at least as large (FIG. 7A) or at least as small (FIG. 7B) as the cross-sectional dimension 422b of the non-threaded portion of the latching lumen 416. In at least some embodiments, the threaded portion 450 has a cross-sectional dimension 430a across opposing ridge peaks that is at least as large (FIG. 7A) or at least as small (FIG. 7B) as the cross-sectional dimension 430b of the non-threaded body 428.

In at least some embodiments, the proximal end of the latching pin 418 includes at least one slot, other recess, protrusion, or the like (not shown) that is shaped to engage an end portion of a tool (for example, a slotted, Phillips, Frearson, square, hex, or star male or female screwdriver, wrench, or the like) to screw the threaded portion 450 into the threaded portion 448. Alternatively, the latching pin 418 of FIGS. 7A and 7B can be coupled to a handle as illustrated in FIG. 6A. Additionally or alternatively, at least one perforation in the attaching element 438 may, when the latching pin 418 is detached from the handle, form at least one slot or other recess in the distal end of the latching pin 418. Additionally or alternatively, the portion 432 forms a protrusion that is shaped to engage the end portion of the tool. In at least some embodiments, the distal end portion of the handle 420 is shaped to form the end portion of the tool (not shown) that corresponds to the shape of the at least one slot, other recess, protrusion, or the like.

Figure 8A:
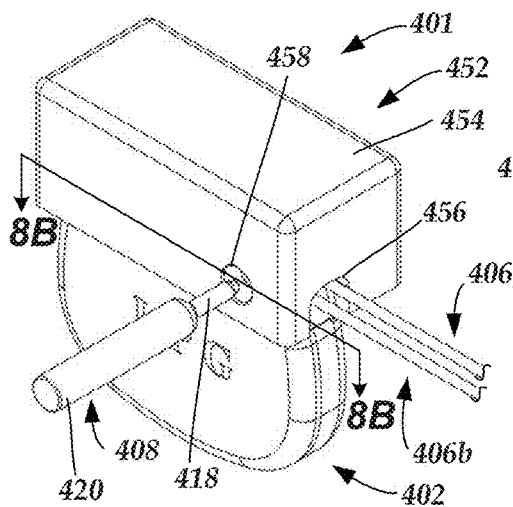
FIG. 8A is a schematic isometric view of another embodiment of the lead latching kit of FIG. 4A, including a pin disposal tool, according to the invention.

It may be desirable to remove a latching pin from the control module 402 to, for example, disconnect one or more of the leads. FIG. 8A is a schematic isometric view of one embodiment of an arrangement 401 including a pin disposal tool 452 for receiving a latching pin 418b from the control module 402. The pin disposal tool 452 has a housing 454 that includes a control module lumen 460 (FIGS. 8B-8D) that can receive at least a portion of the connector housing 412. In at least some embodiments, the housing 454 includes at least one pin engagement port 458 that, when the pin disposal tool 452 is positioned over the connector housing 412, aligns with the latching lumen 416. Optionally, the housing 454 includes at least one lead aperture 456 to receive each lead that extends from the control module 402.

Figure 8B:
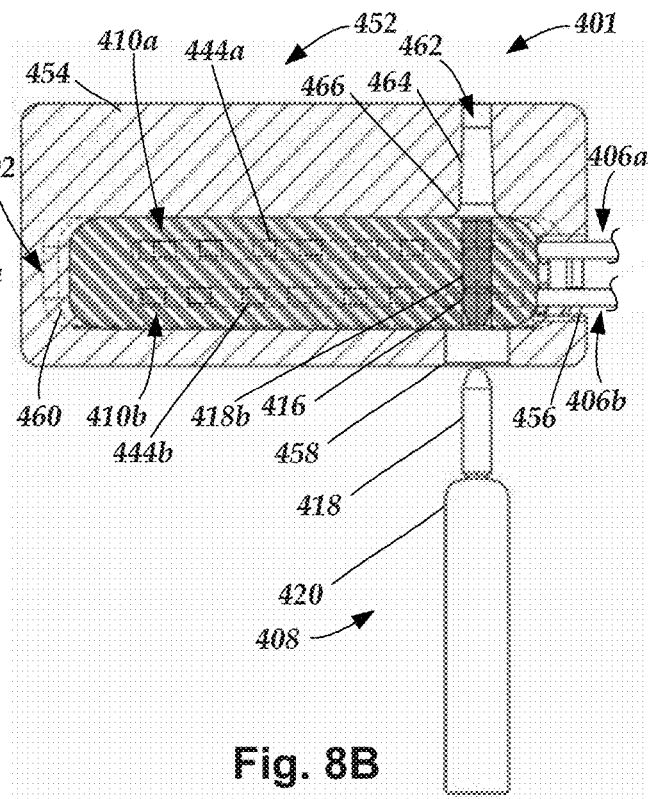
FIG. 8B is a schematic cross-sectional view of one embodiment of the lead latching kit of FIG. 8A taken at line 8B-8B with a latching pin in the connector housing and a latching device positioned to dispose the latching pin into the pin disposal tool, according to the invention.
Figure 8C:
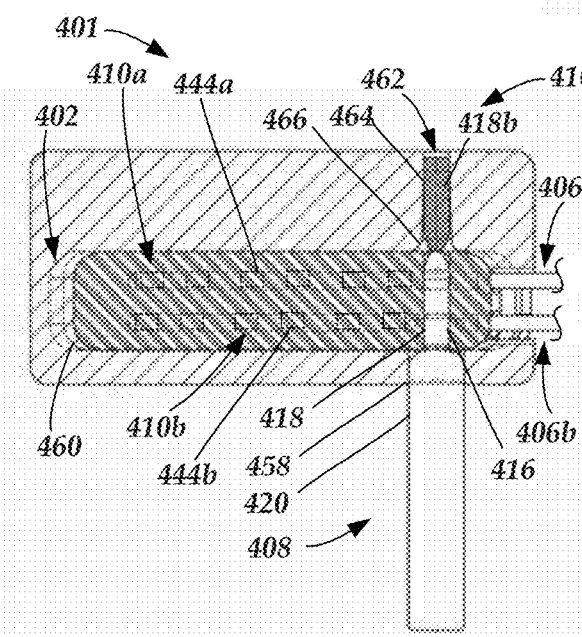
FIG. 8C is a schematic cross-sectional view of one embodiment of the lead latching kit of FIG. 8A taken at line 8B-8B with a latching pin of the latching device positioned in the connector housing after disposing the latching pin into the pin disposal tool, according to the invention.
Figure 8D:
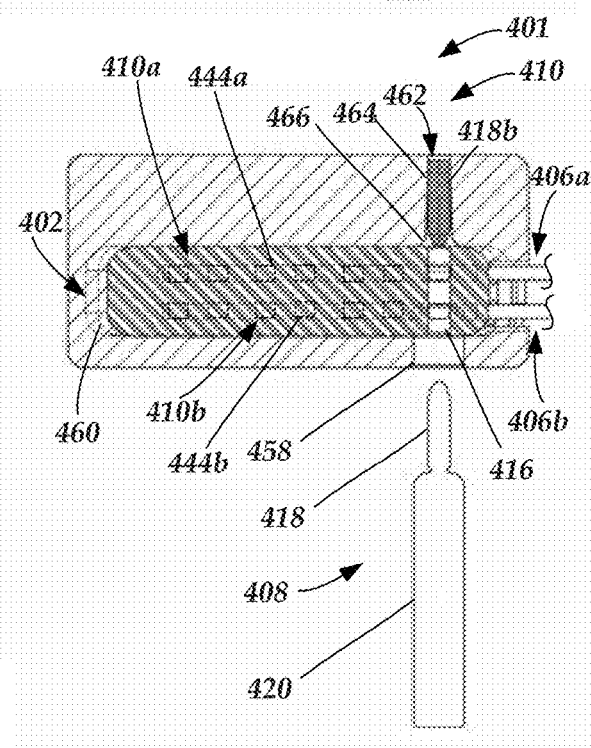
FIG. 8D is a schematic cross-sectional view of one embodiment of the lead latching kit of FIG. 8A taken at line 8B-8B with the latching device removed from the connector housing with the latching pin disposed in the pin disposal tool, according to the invention.

FIGS. 8B-8D are schematic cross-sectional views of one embodiment of the arrangement 401 taken at line 8B-8B. Preferably, the pin disposal tool 452 has a pin catching compartment 462. In at least some embodiments, the pin catching compartment 462 has a tubular body 464 that extends from the control module lumen 460 and that is positioned to align with the latching lumen 416. In at least some embodiments, the pin catching compartment 462 has a tapered opening 466 that faces the control module lumen 460. In at least some embodiments, the pin catching compartment 462 has a cylindrical, cuboid, or other shape. Preferably, the longitudinal dimension of the pin catching compartment 462 is at least as large as the longitudinal dimension of the latching pin 418b. Preferably, the lateral dimension of the pin catching compartment 462 is at least as large as the lateral dimension (for example, diameter) of the latching pin 418b. In at least some embodiments, the control module lumen 460 is shaped to sufficiently seal to the control module 402 to retain the latching pin 418b in the pin catching compartment 462 when removed from the latching lumen 416.

A tool, such as tool 408 or any other suitable tool, is inserted through the pin removal port 458 and into the latching lumen 416 to push the latching pin 418b into the pin catching compartment 462 (FIG. 8C). The latching pin 418 may be removed without detaching the latching pin 418 from the handle 420 (FIG. 8D) to unlatch each lead body 406a, 406b that was compressed by the latching pin 418b. In at least some embodiments, when the lead bodies 406a, 406b have been replaced, repositioned, or the like, the latching pin 418 can be inserted into the latching lumen 416 to latch the lead bodies 406a, 406b and detached from the handle 420b.

The tool 408, latching pin 418, and latching lumen 416 have been illustrated for use with latching leads to a connector 144 of control module 102 or connector 444 of control module 402. It will be understood that the tool 408, latching pin 418, and latching lumen 416 can be adapted and used with other lead connectors (for example, connector 322 of FIG. 3B), such as those used on lead extensions, adapters, and the like, to latch the leads within the connector. In addition, the tool 408, latching pin 418, and latching lumen 416 can be adapted and used for a lead anchor (which is a type of connector that attaches to a portion of the lead with the lead extending out of opposite sides of the connector of the lead anchor) to latch one or more leads to the lead anchor.

Figure 9:
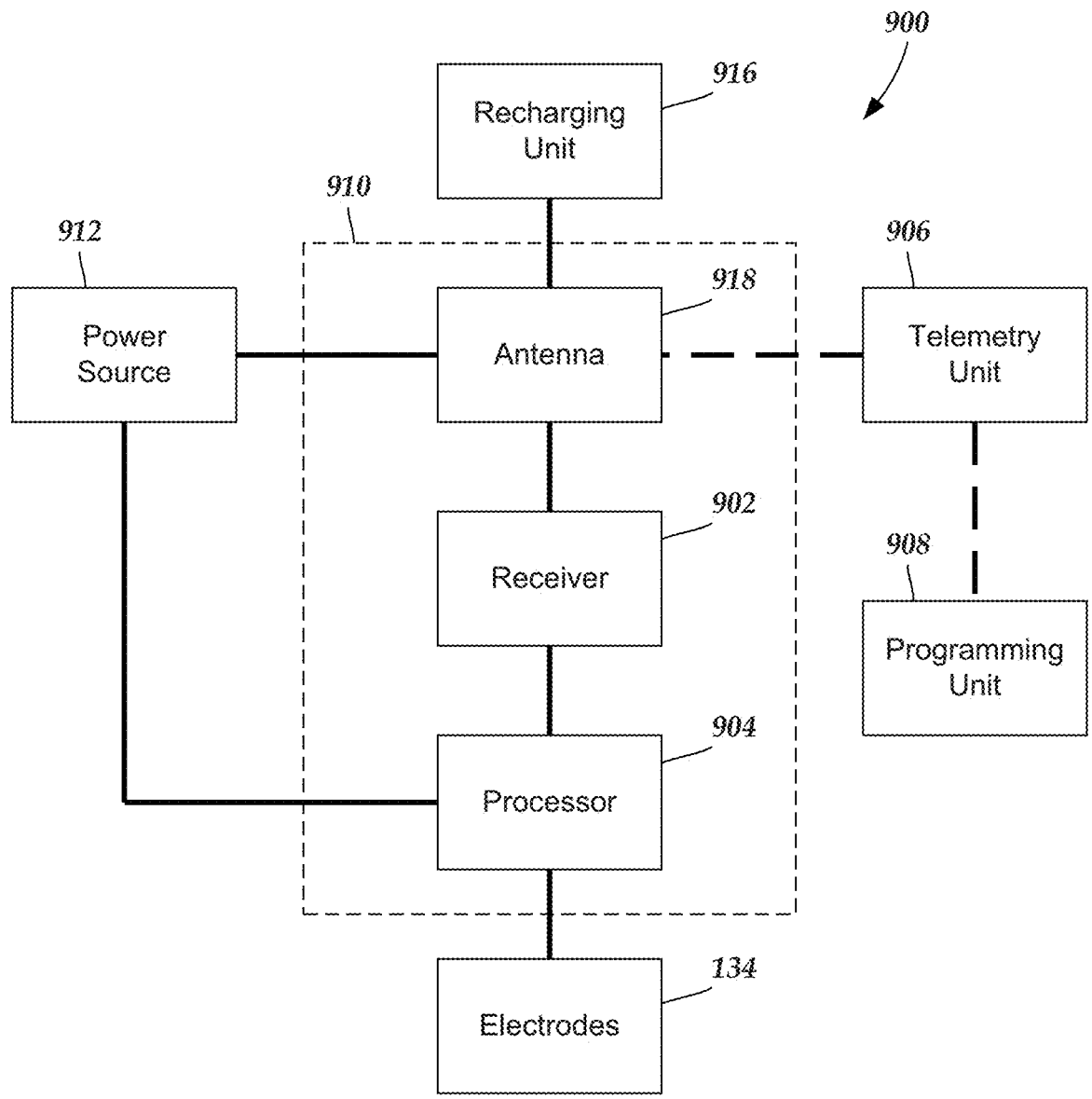
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on at least one circuit board or similar carrier within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control at least one of the timing, frequency, strength, duration, and waveform of the pulses. In addition, the processor 904 can select which electrodes can be used to provide stimulation, if desired. In at least some embodiments, the processor 904 selects which electrode(s) are cathodes and which electrode(s) are anodes. In at least some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (for example, RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying at least one of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification provides a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead latching kit, comprising:
   a connector comprising a housing that defines a lead lumen and a latching lumen that at least partially intersects the lead lumen, wherein the lead lumen is configured to receive a portion of an electrical stimulation lead or lead extension; and
   a latching device comprising a latching pin, a handle, and an attaching element that physically attaches and fastens the latching pin to the handle, wherein the latching pin has a longitudinal surface and is configured for insertion into the latching lumen and the attaching element is configured to enable the latching pin to detach from the handle when the latching pin is in the latching lumen, wherein the latching pin has a cross-sectional dimension so that, when the latching pin is positioned in the latching lumen and the portion of the electrical stimulation lead or lead extension is positioned in the lead lumen, the longitudinal surface of the latching pin engages the portion of the electrical stimulation lead or lead extension to latch the electrical stimulation lead or lead extension to the connector, wherein the latching pin is a modified cylinder with a rounded, longitudinal surface and one flat, longitudinal surface.

2. The electrical stimulation lead latching kit of claim 1, wherein the housing of the connector comprises at least two lead lumens that each at least partially intersect the latching lumen.

3. The electrical stimulation lead latching kit of claim 1, wherein the latching lumen has a longitudinal dimension that is at least as long as a longitudinal dimension of the latching pin.

4. The electrical stimulation lead latching kit of claim 1, wherein the latching pin has a tapered proximal end portion.

5. The electrical stimulation lead latching kit of claim 1, wherein at least one portion of the latching lumen is threaded and a portion of the latching pin is also threaded.

6. The electrical stimulation lead latching kit of claim 1, wherein an end of the latching pin comprises a recess configured to receive an end portion of a tool.

7. The electrical stimulation lead latching kit of claim 1, wherein the housing includes another lead lumen that at least partially intersects the latching lumen and is disposed opposite the lead lumen with the latching lumen between the lead lumen and the other lead lumen.

8. The electrical stimulation lead latching kit of claim 1, wherein the latching pin has the cross-sectional dimension so that, when the latching pin is positioned in the latching lumen and the portion of the electrical stimulation lead or lead extension is positioned in the lead lumen, the latching pin compresses the portion of the electrical stimulation lead or lead extension to latch the electrical stimulation lead or lead extension to the connector.

9. The electrical stimulation lead latching kit of claim 1, further comprising the electrical stimulation lead, wherein the electrical stimulation lead comprises
   a lead body having a distal end portion, a proximal end portion, and a longitudinal length;
   a plurality of electrodes disposed along the distal end portion of the lead body;
   a plurality of terminals disposed along the proximal end portion of the lead body; and
   a plurality of conductors electrically coupling the terminals to the electrodes.

10. The electrical stimulation lead latching kit of claim 1, wherein the housing of the connector includes another latching lumen that at least partially intersects the lead lumen.

11. The electrical stimulation lead latching kit of claim 1, further comprising a control module wherein the control module comprises the connector.

12. The electrical stimulation lead latching kit of claim 11, further comprising a pin disposal tool that includes a housing, the housing of the pin disposal tool including a control module lumen and a pin catching compartment that extends from the control module lumen, wherein the control module lumen is configured to receive the housing of the connector, wherein the pin catching compartment is configured to at least partially align with the latching lumen of the housing of the connector when the control module lumen receives the housing of the connector, wherein the pin catching compartment is further configured to receive the latching pin from the latching lumen of the housing of the connector when the pin catching compartment at least partially aligns with the latching lumen of the housing of the connector.

13. A method of unlatching an electrical stimulation lead or lead extension using the electrical stimulation lead latching kit of claim 12, the method comprising:
   providing the control module of the electrical stimulation lead latching kit with a portion of the electrical stimulation lead or lead extension inserted in the lead lumen and the latching pin disposed in the latching lumen and engaging the portion of the electrical stimulation lead or lead extension;
   inserting the housing of the connector into the control module lumen of the pin disposal tool to at least partially align the pin catching compartment of the pin disposal tool with the latching lumen of the housing of the connector; and
   pushing the latching pin from the latching lumen into the pin catching compartment of the pin disposal tool to disengage the latching pin from the portion of the electrical stimulation lead or lead extension to unlatch the electrical stimulation lead or lead extension.

14. The electrical stimulation lead latching kit of claim 1, further comprising a lead extension, wherein the lead extension comprises the connector.

15. The electrical stimulation lead latching kit of claim 1, further comprising a lead anchor, wherein the lead anchor comprises the connector.

16. A method of latching an electrical stimulation lead or lead extension using the electrical stimulation lead latching kit of claim 1, the method comprising:
   inserting a portion of the electrical stimulation lead or lead extension into the lead lumen of the housing of the connector of the electrical stimulation lead latching kit;
   inserting the latching pin of the latching device into the latching lumen of the housing of the connector to engage the electrical stimulation lead or lead extension to latch the electrical stimulation lead or lead extension to the connector; and
   detaching the latching pin from the handle while the latching pin is positioned in the latching lumen.

17. A connector, comprising:
  a housing that defines a lead lumen, a latching lumen that at least partially intersects the lead lumen, and a latching lumen axis extending along a center of the latching lumen, wherein the lead lumen is configured to receive a portion of an electrical stimulation lead or lead extension; and
  a latching pin disposed in the latching lumen, wherein the latching pin has a longitudinal surface that is parallel to the latching lumen axis and is configured for rotation between an unlocked position and a locked position, wherein, in the unlocked position, the connector is configured for insertion or removal of a portion of the electrical stimulation lead or lead extension from the lead lumen and, in the locked position with the portion of the electrical stimulation lead or lead extension disposed in the lead lumen, the longitudinal surface of the latching pin engages the portion of the electrical stimulation lead or lead extension to latch the electrical stimulation lead or lead extension to the connector.

18. The connector of claim 17, wherein the housing comprises at least two lead lumens that each at least partially intersect the latching lumen.

\* \* \* \* \*